United States Patent [19]

Lambert

[11] Patent Number: 4,967,743

[45] Date of Patent: Nov. 6, 1990

[54] NEONATAL CLOSED SYSTEM FOR INVOLUNTARY ASPIRATION AND VENTILATION, AND METHOD

[75] Inventor: Richard C. Lambert, Lehi, Utah

[73] Assignee: Ballard Medical Products, Midvale, Utah

[21] Appl. No.: 279,488

[22] Filed: Dec. 1, 1988

Related U.S. Application Data

[62] Division of Ser. No. 157,237, Feb. 18, 1988, Pat. No. 4,838,255, which is a division of Ser. No. 24,436, Mar. 11, 1987, Pat. No. 4,825,859.

[51] Int. Cl.$^5$ ............................................. A61M 15/00
[52] U.S. Cl. ........................... 128/202.16; 128/207.16; 604/905
[58] Field of Search ....................... 128/207.14, 207.15, 128/207.16, 207.17, 202.13, 202.16, 912; 604/119, 283, 905, 243

[56] References Cited

U.S. PATENT DOCUMENTS

| | | |
|---|---|---|
| 274,447 | 3/1883 | Kennish . |
| 580,574 | 4/1897 | Fowler . |
| 1,120,549 | 12/1914 | Schellberg . |
| 1,463,735 | 7/1923 | Varrieur ............................... 251/100 |
| 1,672,114 | 6/1928 | Crow . |
| 1,917,981 | 7/1933 | Kindl ................................... 251/95 |
| 1,944,553 | 1/1934 | Freund ................................ 128/229 |
| 2,187,586 | 1/1940 | Hooper ............................... 128/224 |
| 2,212,334 | 8/1940 | Wallerich ........................... 604/280 |
| 2,584,450 | 2/1952 | Holt et al. ........................... 128/203 |
| 2,705,959 | 4/1955 | Elmore ................................ 128/351 |
| 2,755,060 | 7/1956 | Twyman ............................. 251/342 |
| 2,893,395 | 7/1959 | Buck .................................... 128/349 |
| 2,912,982 | 11/1959 | Barsky ................................. 128/912 |
| 2,937,643 | 5/1960 | Elliot ................................... 128/214 |
| 3,017,880 | 1/1962 | Brook .................................... 128/29 |
| 3,039,463 | 6/1962 | Dickey, Jr. et al. ................ 128/912 |
| 3,070,132 | 12/1962 | Sheridan ............................. 604/280 |
| 3,175,557 | 3/1965 | Hammond ....................... 128/207.14 |
| 3,322,126 | 5/1967 | Rüsch et al. ........................ 128/351 |
| 3,335,723 | 8/1967 | Waldman, Jr. .................... 128/214.4 |
| 3,363,629 | 1/1968 | Kuhn ................................... 604/281 |
| 3,444,860 | 5/1969 | Harrell ................................ 128/349 |

(List continued on next page.)

FOREIGN PATENT DOCUMENTS

8307517A1 9/1984 Fed. Rep. of Germany .
560910 7/1924 France .

OTHER PUBLICATIONS

A New Controllable Suction Catheter for Blind Cannulation of the Main Stem Bronchi, *Critical Care Medicine*, vol. 6, No. 5, Sep.–Oct. 1978.

(List continued on next page.)

*Primary Examiner*—Max Hindenburg
*Assistant Examiner*—John P. Lacyk
*Attorney, Agent, or Firm*—Lynn G. Foster

[57] ABSTRACT

Apparatus for respiratory therapy, which is particularly useful in a neonatal context, and related methods, the apparatus comprising an adaptor for connection to the exposed fitting of an indwelling endotracheal tube of any one of several types to an aspirating apparatus which may include ventilating capacity. The adaptor includes an appendage by which a lavage solution can be selectively introduced into the lungs of a patient through the indwelling endotracheal tube to loosen secretions without necessarily interrupting the ventilation cycle or requiring that the ventilating circuit be broken. The apparatus also comprises a fitting at one end of an aspirating/ventilating apparatus which has low dead space, alleviating the incidence of inadvertent disconnection and trauma induced by unintended displacement of the end fitting and accommodating not only aspiration and ventilation but also monitoring of certain vital indicators to allow prompt medical response to contraindications. The apparatus further comprises a manual stationary insertion guide for introduction of the suction catheter tube into the respiratory system of the patient and control stop structure which accommodates insertion into the respiratory system of the patient of only a predetermined length of the suction catheter tube. The apparatus also comprises structure by which the flow of secretions through the suction catheter tube can be visually monitored.

9 Claims, 5 Drawing Sheets

U.S. PATENT DOCUMENTS

| | | | |
|---|---|---|---|
| 3,461,877 | 8/1969 | Morch | 128/351 |
| 3,485,234 | 12/1969 | Stevens | 604/281 |
| 3,508,554 | 4/1970 | Sheridan | 604/280 |
| 3,517,669 | 6/1970 | Buono et al. | 128/276 |
| 3,595,445 | 7/1971 | Buford et al. | 222/213 |
| 3,605,750 | 4/1969 | Sheridan et al. | 604/280 |
| 3,612,038 | 10/1971 | Halligan | 604/281 |
| 3,628,532 | 12/1971 | Magrath | 128/145.8 |
| 3,633,758 | 1/1972 | Moise | 604/281 |
| 3,719,737 | 3/1973 | Vaillancourt | 604/281 |
| 3,730,179 | 5/1973 | Williams | 128/145.5 |
| 3,734,094 | 5/1973 | Calinog | 128/2.06 |
| 3,757,771 | 9/1973 | Ruegg et al. | 128/2.1 E |
| 3,774,604 | 11/1973 | Danielsson | 128/214.4 |
| 3,825,001 | 7/1974 | Bennet et al. | 128/214.4 |
| 3,885,561 | 5/1975 | Cami | 604/280 |
| 3,894,540 | 7/1975 | Bonner, Jr. | 128/349 R |
| 3,911,919 | 10/1975 | Raitto | 128/276 |
| 3,935,857 | 2/1976 | Co | 604/281 |
| 3,937,220 | 2/1976 | Coyne | 604/119 |
| 3,991,762 | 11/1976 | Radford | 128/207.16 |
| 4,015,336 | 4/1977 | Johnson | 32/33 |
| 4,022,219 | 5/1977 | Basta | 128/351 |
| 4,027,659 | 6/1977 | Slingluff | 604/280 |
| 4,036,210 | 7/1977 | Campbell et al. | 128/2 F |
| 4,047,527 | 9/1977 | Kelsen | 128/229 |
| 4,050,667 | 9/1977 | Kossett | 604/281 |
| 4,052,990 | 10/1977 | Dodgson | 128/351 |
| 4,062,363 | 12/1977 | Bonner, Jr. | 128/349 |
| 4,081,176 | 3/1978 | Johnson | 251/342 |
| 4,119,101 | 10/1978 | Igich | 128/351 |
| 4,152,017 | 5/1979 | Abramson | 285/260 |
| 4,170,996 | 10/1979 | Wu | 128/349 R |
| 4,193,406 | 3/1980 | Jinotti | 128/204.18 |
| 4,212,300 | 7/1980 | Meals | 128/276 |
| 4,225,371 | 9/1980 | Taylor et al. | 156/652 |
| 4,235,232 | 11/1980 | Spaven et al. | 128/214.4 |
| 4,240,417 | 12/1980 | Holever | 128/203 |
| 4,245,636 | 1/1981 | Sparks et al. | 128/214 R |
| 4,256,099 | 3/1981 | Dryden | 128/200.26 |
| 4,275,724 | 6/1981 | Behrstock | 604/281 |
| 4,300,550 | 11/1981 | Gandi et al. | 128/207.18 |
| 4,324,239 | 4/1982 | Gordon et al. | 128/274 |
| 4,326,520 | 4/1982 | Alley | 128/214.4 |
| 4,327,723 | 5/1982 | Frankhouser | 128/214.4 |
| 4,327,735 | 5/1982 | Hampson | 128/348 |
| 4,356,610 | 11/1982 | Hon et al. | 29/157 |
| 4,387,879 | 6/1983 | Tauschinski | 251/149.1 |
| 4,397,442 | 8/1983 | Larkin | 251/342 |
| 4,414,999 | 11/1983 | Basta | 137/240 |
| 4,426,062 | 1/1984 | Bowrom | 251/7 |
| 4,440,378 | 4/1984 | Sullivan | 251/117 |
| 4,451,257 | 5/1984 | Atchley | 604/119 |
| 4,456,223 | 6/1984 | Ebling | 251/342 |
| 4,457,487 | 7/1984 | Steigerwald | 251/117 |
| 4,459,982 | 7/1984 | Fry | 128/204.23 |
| 4,469,483 | 9/1984 | Becker et al. | 128/DIG. 21 |
| 4,497,468 | 2/1985 | Hubbard et al. | 251/117 |
| 4,534,542 | 8/1985 | Russo | 251/342 |
| 4,537,387 | 8/1985 | Danby et al. | 251/331 |
| 4,569,344 | 2/1986 | Palmer | 128/207.16 |
| 4,595,005 | 6/1986 | Jinotti | 128/205.24 |
| 4,632,112 | 12/1986 | Matthews | 128/305.3 |
| 4,655,752 | 4/1987 | Honkanen et al. | 604/256 |
| 4,671,291 | 6/1987 | Wilson | 604/280 |
| 4,673,393 | 6/1987 | Suzuki et al. | 604/167 |
| 4,696,305 | 9/1987 | von Berg | 128/673 |
| 4,703,775 | 11/1987 | Pastrone | 137/625.3 |
| 4,704,111 | 11/1987 | Moss | 604/280 |

OTHER PUBLICATIONS

Evaluation of Selective Bronchial Suctioning Techniques Used for Infants and Children, *Anesthesiology*, 48:379–380.

Selective Brochial Suctioning in the Adult Using a Curved-Tipped Catheter with a Guide Mark, *Critical Care Medicine*, vol. 10, No. 11, Nov. 1982.

Selective Tracheobronchial Aspiration, *Thorax*, 32, 346–348, 1977.

Device for Determining Location of an Endotracheal Catheter Tip, *Critical Care Medicine*, vol. 12, No. 2, Feb. 1984.

Design and Function of Tracheal Suction Catheters, 1982.

The New NL Tracheal Suction Catheter, *Anesthesiology*, 1982.

Comparison of Tracheobrinchial Suction Catheters in Humans, Chest, vol. 69, pp. 179–181, Feb. 1976.

The Bear NVM-1 Neonatal Volume Monitor, 1986 [citing U.S. Pat. No. 4,363,238].

Side Eye Position—Davol literature.

Cathmark, item of literature.

Prevention of Hypoxic Complication, 1968.

Disposable Suction Catheter, *Nursing*, May 1979.

Suctioning of Left Bronchial Tree in the Intubated Adult, *Care Medicine*, Kamiaru; 092.

Evaluation of Selective Bronchial Suctioning in the Adult, *Critical Care Medicine*, vol. 8, No. 12, 1980.

ACMI Catalog, pp. 31–35, Copyright 1960.

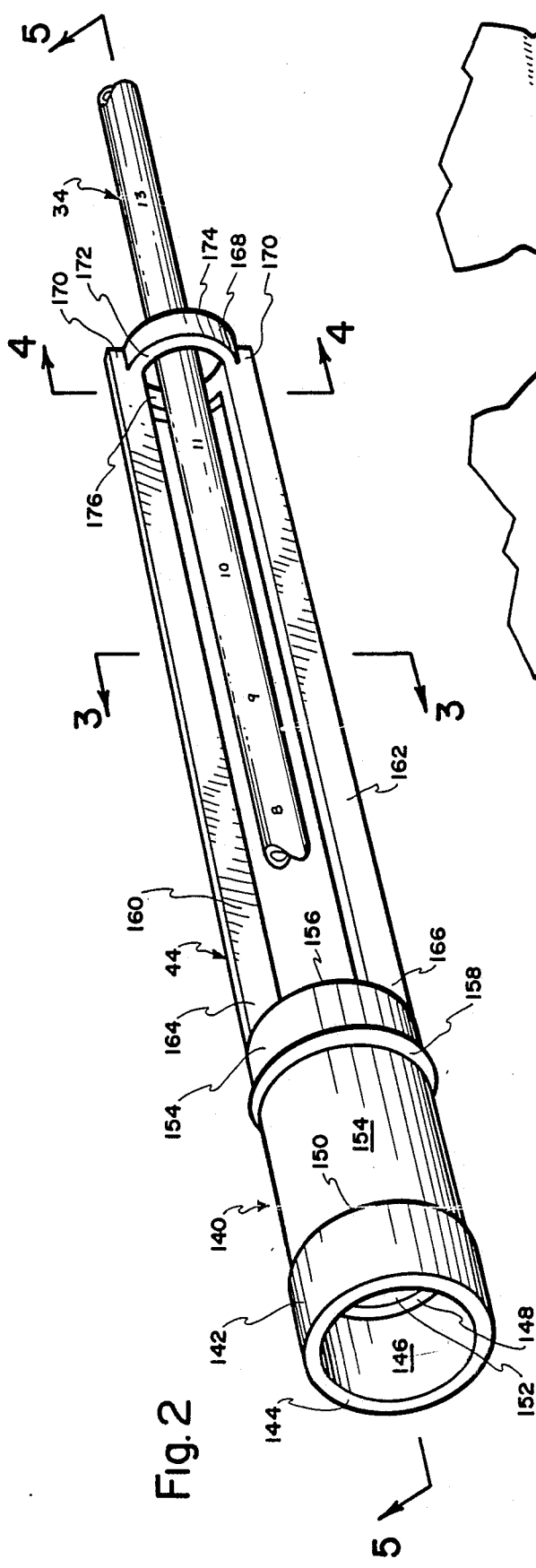
Fig. 2
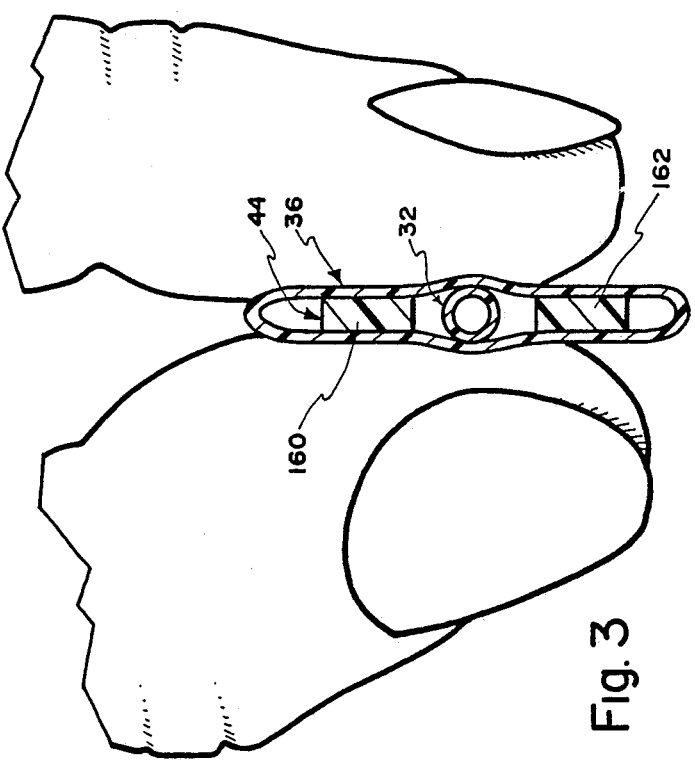
Fig. 3
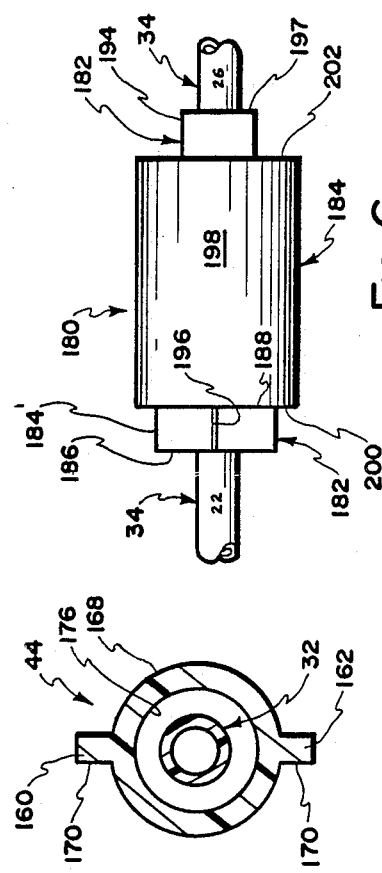
Fig. 6
Fig. 4

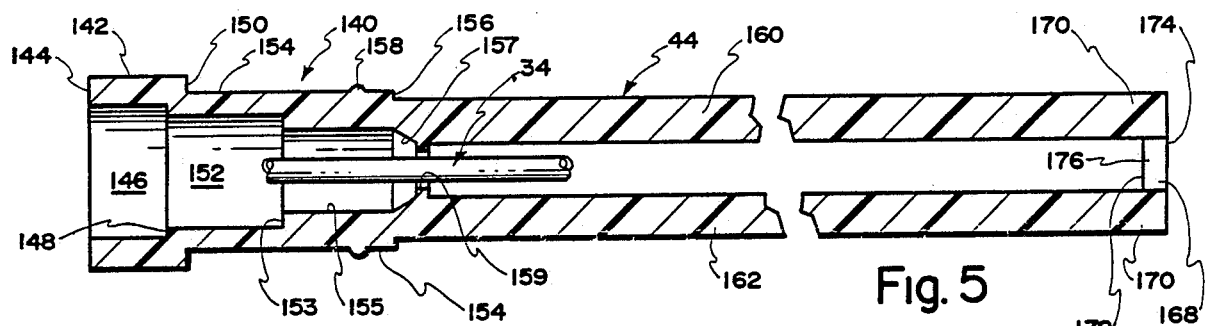
Fig. 5
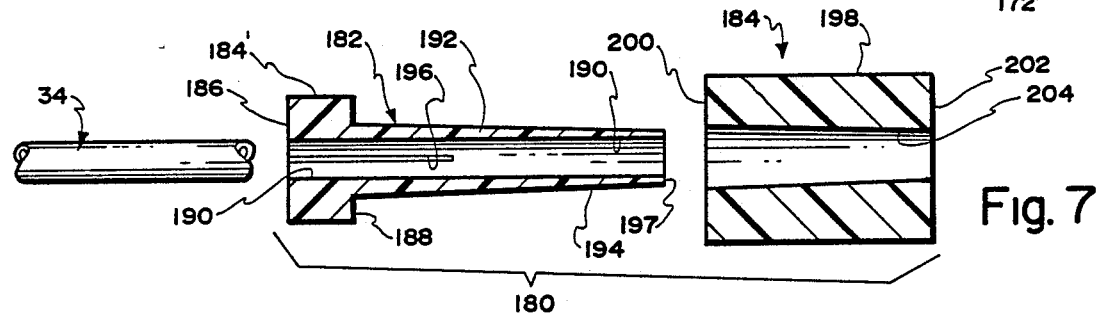
Fig. 7
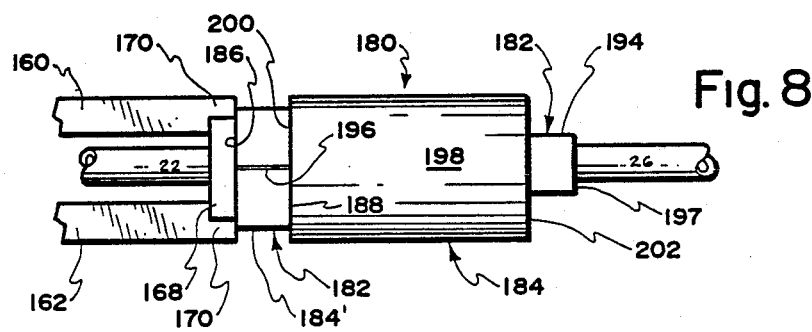
Fig. 8
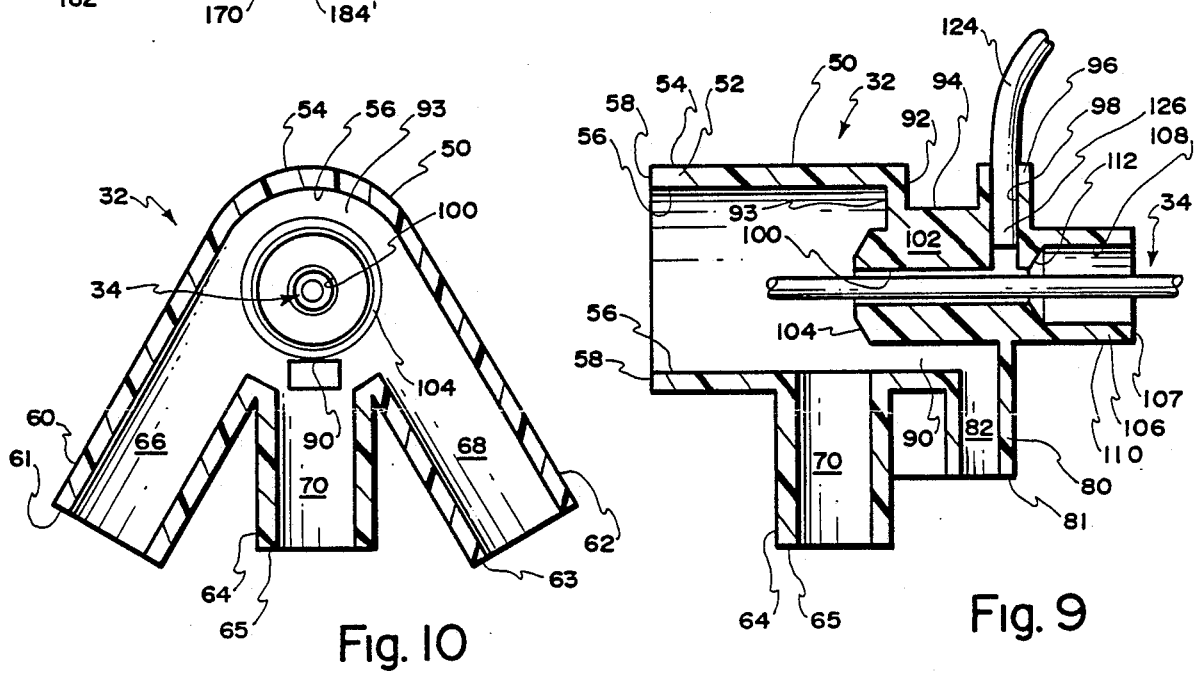
Fig. 10
Fig. 9

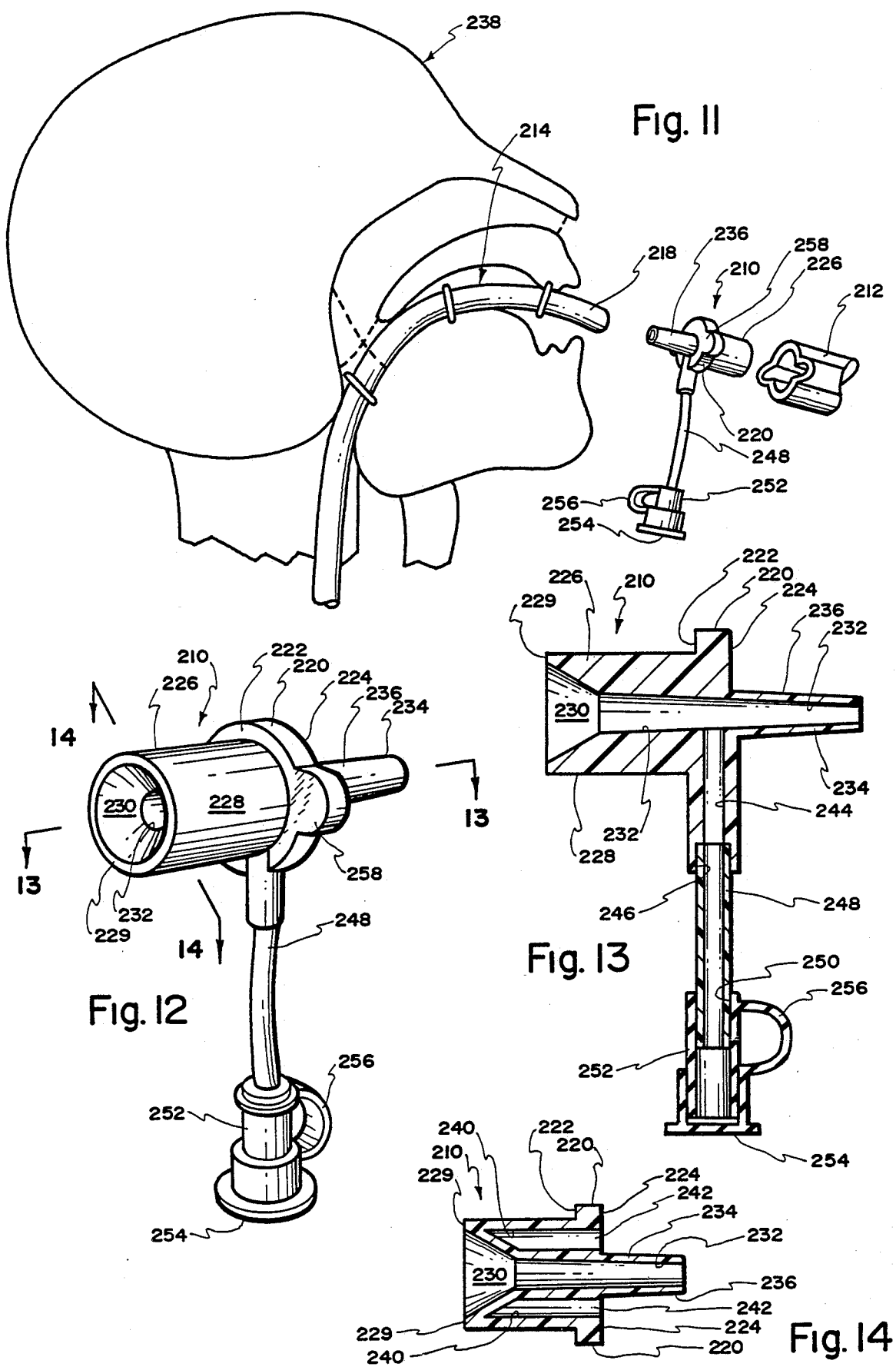

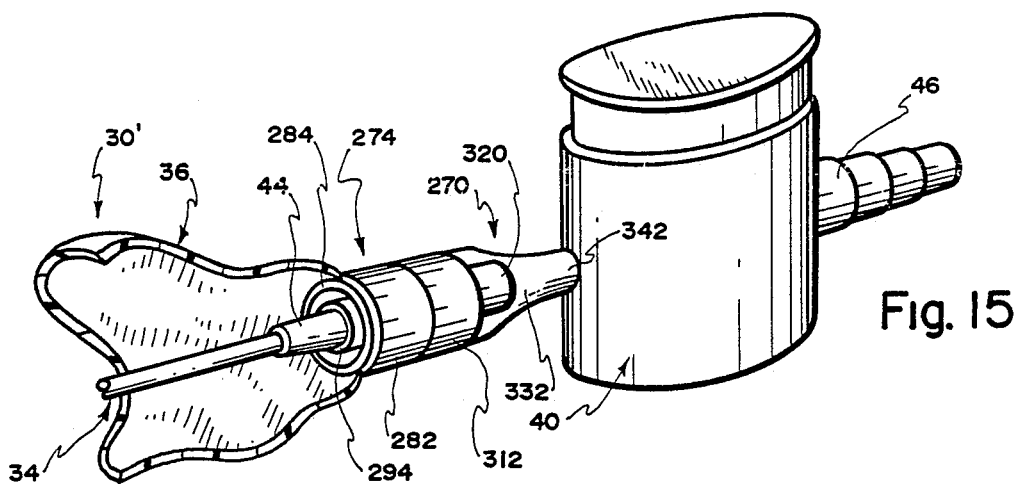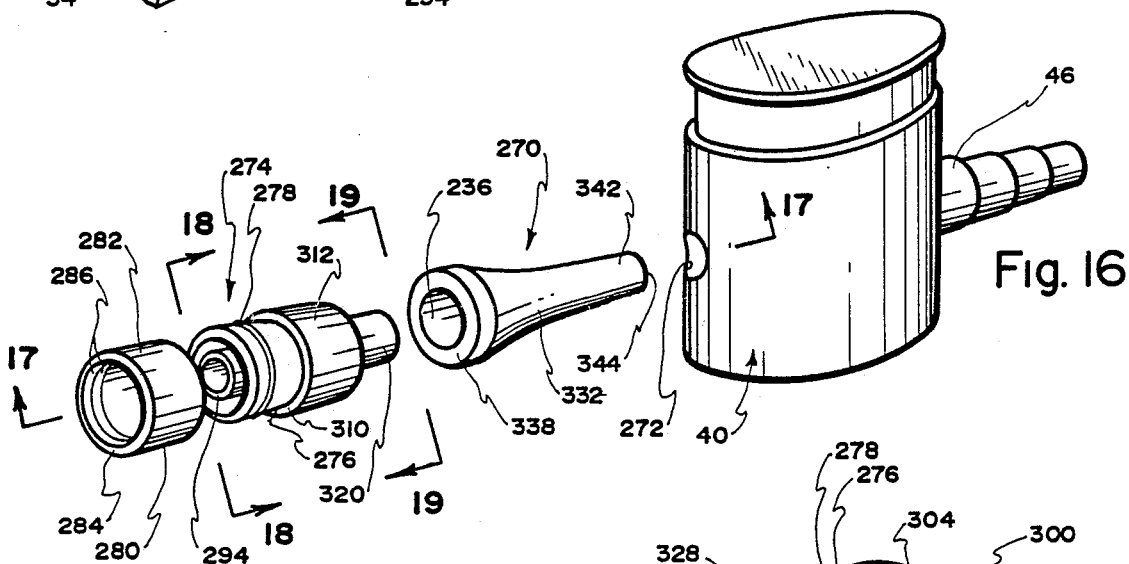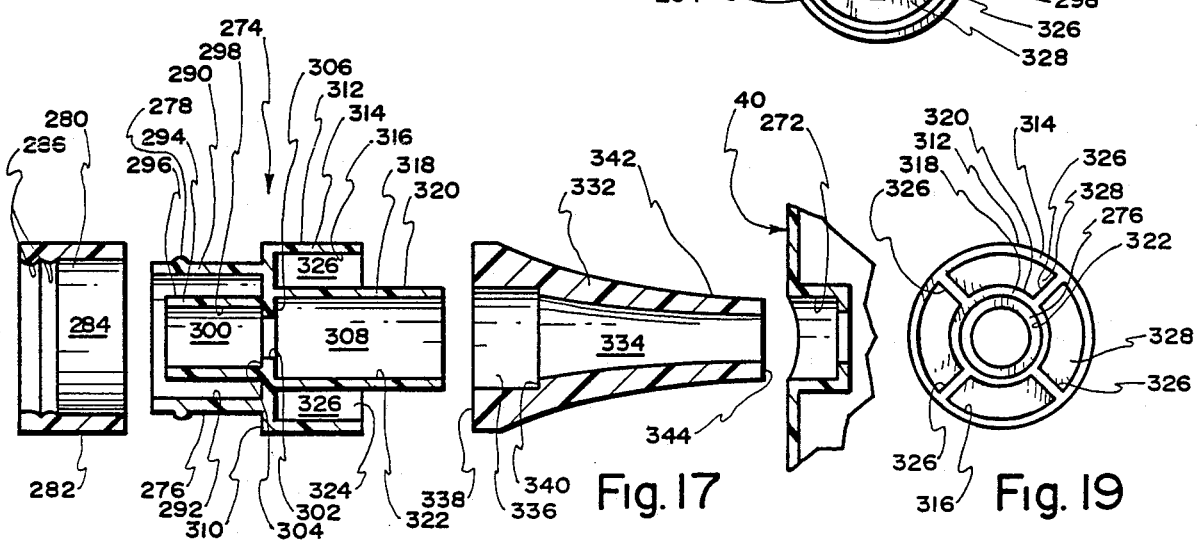

NEONATAL CLOSED SYSTEM FOR INVOLUNTARY ASPIRATION AND VENTILATION, AND METHOD

CONTINUITY

This application is a division of my copending U.S. patent application Ser. No. 157,237, filed Feb. 18, 1988, now U.S. Pat. No. 4,838,255, which is a division of U.S. patent application Ser. No. 24,436, filed Mar. 11, 1987, now U.S. Pat. No. 4,825,859.

FIELD OF THE INVENTION

The present invention relates generally to involuntary ventilation of the respiratory system of a medical patient and involuntary aspiration of secretions from the lungs of the patient and more particularly to a novel neonatal suctioning device, and related method, the device being used in conjunction with an indwelling endotracheal tube typically placed, for example, in the throat of a newborn infant by which accumulated secretions are selectively evacuated from the lungs of the infant without injury to the infant.

PRIOR ART

Respiratory distress frequently occurs in infants and small children experiencing respiratory problems. This is commonplace in premature infants. When an infant or small child is unable to breathe adequately on its own, intubation and involuntary ventilation is provided via an endotracheal tube. This requires periodic, involuntary removal, via a small suction catheter tube, of secretions which accumulate in the lungs, without injury to or penetration of the lungs with the suction catheter tube. Precise control in placement of the suction catheter tube is also of great concern because of the risk of trauma, and injury, during placement. Bulky paraphernalia can incumber movement of the child and be the source of injury to the child, for example, if caught in the bed clothing of the child. Also, adaption for otherwise incompatible endotracheal and ventilating and aspirating equipment from different sources has not heretofore been available. Furthermore, the option of introduction of a lavage solution into the lungs to loosen secretions without breaking the ventilation circuit has not been satisfactorily addressed heretofore.

Monitoring of certain vital medical information and the efficacy of the secretion removal process are important, so that any contraindication on the part of the child can be medically addressed without delay.

None of the neonatal ventilating/aspirating devices proposed by the prior art address the problems associated with proper medical care for infants and small children.

The most relevant, known aspirating/ventilating prior art patents are U.S. Pat. Nos. 3,991,762 and 4,569,344. These do not per se address the aforementioned neonatal needs. In each case, an essentially linear catheter tube is provided for insertion into and removal of secretions from the lungs of a medical patient.

The literature, with one exception, does not address neonatal needs, but discloses straight-tip, curved-tip and angled-tip suction catheters, use of guide marks, in the form of dots, together with radiopaque liquid for catheter tip placement, control of the length of the catheter to prevent kinking and avoidance of catheter rotation during placement.

The literature also discloses single-use, non-ventilating devices, one example of which is Davol's aspirating catheter assembly, which comprises a sterile bag, a catheter tube within the bag and a vent fitting at the proximal end of the assembly, which is operated to aspirate by placing a thumb or finger over an atmospheric vent port.

The one neonatal aspirating/ventilating device disclosed in the literature includes expensive electronic gear, comprises bulky, high dead space components and does not provide facile and accurate control for periodic suction catheter tube placement in the lungs of a child.

BRIEF SUMMARY AND OBJECTS OF THE PRESENT INVENTION

In brief summary, the present invention is intended to overcome or substantially alleviate the aforementioned limitations of the prior art and comprises a novel apparatus for respiratory therapy, which is particularly useful in a neonatal context and related methods.

Features of the present invention which are noteworthy include: (a) provision for facile, injury-free and accurate placement of an aspirating suction catheter tube in the desired location within the respiratory system of the patient; (b) compatible adaption interposed between the exposed fitting of an indwelling endotracheal tube of any one of several types and an aspirating apparatus or an aspirating/ventilating apparatus; (c) provision of an adaptor by which a lavage solution can be selectively introduced into the lungs of a patient through an existing indwelling endotracheal tube to loosen secretions without necessarily interrupting the ventilation cycle or requiring that the ventilating circuit be broken; (d) a novel fitting at one end of an aspirating-/ventilating apparatus which has low dead space, alleviating the incidences of inadvertent disconnection and trauma induced by unintended displacement of the fitting and accommodating not only aspiration and ventilation but also monitoring of certain vital indicators to allow prompt medical response to contraindications; (e) an insertion guide for the suction catheter tube; (f) control structure which accommodates insertion into the respiratory system of the patient of only a predetermined length of the suction catheter tube; and (g) structure by which the flow of secretions through a suction catheter tube can be visually monitored.

With the foregoing in mind, it is a primary object of the present invention to provide a novel apparatus for respiratory therapy, which is particularly useful in a neonatal context, and a related method.

It is a further important object of the present invention to provide apparatus for respiratory therapy which accommodates facile, accurate and injury-free placement of an aspirating suction catheter tube in a desired location within the respiratory system of a patient.

A further dominant object of the present invention is the provision of a novel adaptor to be interposed between an exposed fitting of an indwelling endotracheal tube of any one of several types and an aspirating apparatus or an aspirating/ventilating apparatus to accommodate aspiratory therapy or aspiratory/respiratory therapy.

A further paramount object of the present invention is the provision of a novel adaptor by which a lavage solution can be selectively introduced into the lungs of a patient through an existing indwelling endotracheal tube to loosen secretions within the lungs without necessarily interrupting the ventilation cycle or requiring that the ventilating circuit be broken.

A further object of significance is the provision of a novel fitting at one end of an aspirating/ventilating apparatus which has low dead space, alleviates the incidence of inadvertent disconnection and trauma induced by unintended displacement of the fitting and accommodates not only aspiration and ventilation but also the monitoring of certain vital patient indicators to allow prompt medical response to contraindications.

An additional dominant object of the present invention is the provision of an insertion guide for a suction catheter tube of an aspirating or aspirating/ventilating apparatus;

A further object of significance is the provision of control structure in association with a suction catheter tube which accommodates insertion into the respiratory system of the patient of only a predetermined length of the catheter tube to thereby prevent lung injury.

Another object of importance is the provision of structure by which the flow of secretions being removed from a selected lung of a patient through a suction catheter tube can be accurately visually monitored.

These and other objects and features of the present invention will be apparent from the detailed description taken with reference to the accompanying drawings.

BRIEF DESCRIPTION OF THE DRAWINGS

FIG. 2 is an enlarged perspective representation of the insertion guide for the suction catheter tube of the apparatus of FIG. 1 with the collapsible envelope removed;

FIG. 3 is a cross-section taken along lines 3—3 of FIG. 2 showing the external collapsible envelope and the suction catheter tube held between two fingers of the user, showing the preferred mode of insertion of the suction catheter tube into the respiratory system of a patient using the insertion guide;

FIG. 4 is a cross-section taken lines 4—4 of FIG. 2;

FIG. 5 is a cross-section taken along lines 5—5 of FIG. 2;

FIG. 6 is a side elevation view of a suction catheter tube insertion control device compressively assembled at a predetermined location along the exterior of the suction catheter tube;

FIG. 7 is an exploded cross-sectional view of the components of the suction catheter tube insertion control device of FIG. 6;

FIG. 8 is a side elevation view of the suction catheter tube control device of FIG. 6 in its locked condition illustrated as having reached its stop site where the insertion control device engages the trailing end of the suction catheter tube insertion guide;

FIG. 9 is a cross-section taken along lines 9—9 of FIG. 1;

FIG. 10 is a cross-section taken along lines 10—10 of FIG. 1;

FIG. 11 is an exploded fragmentary perspective of a further embodiment of the present invention in the form of an adaptor interposed between an exposed fitting of an indwelling endotracheal tube and an aspirating or aspirating/ventilating apparatus to accommodate introduction of a lavage solution into the lungs of a patient to loosen accumulated secretions;

FIG. 12 is an enlarged perspective of the adaptor of FIG. 11, the orientation of which is reversed in comparison with FIG. 11;

FIG. 13 is a cross-section taken along lines 13—13 of FIG. 12;

FIG. 14 is a cross-section taken along lines 14—14 of FIG. 12;

FIG. 15 illustrates in fragmentary perspective a further embodiment of the present invention in the form of a secretion removal observation chamber interposed between the trailing end of a suction catheter tube and a control valve;

FIG. 16 is an exploded perspective representation of the embodiment of the present invention of FIG. 15;

FIG. 17 is a cross-section taken along the lines 17—17 of FIG. 16;

FIG. 18 is an end view taken along lines 18—18 of FIG. 16; and

FIG. 19 is and end view taken along lines 19—19 of FIG. 16.

DETAILED DESCRIPTION OF THE ILLUSTRATED EMBODIMENTS

Figure 1:
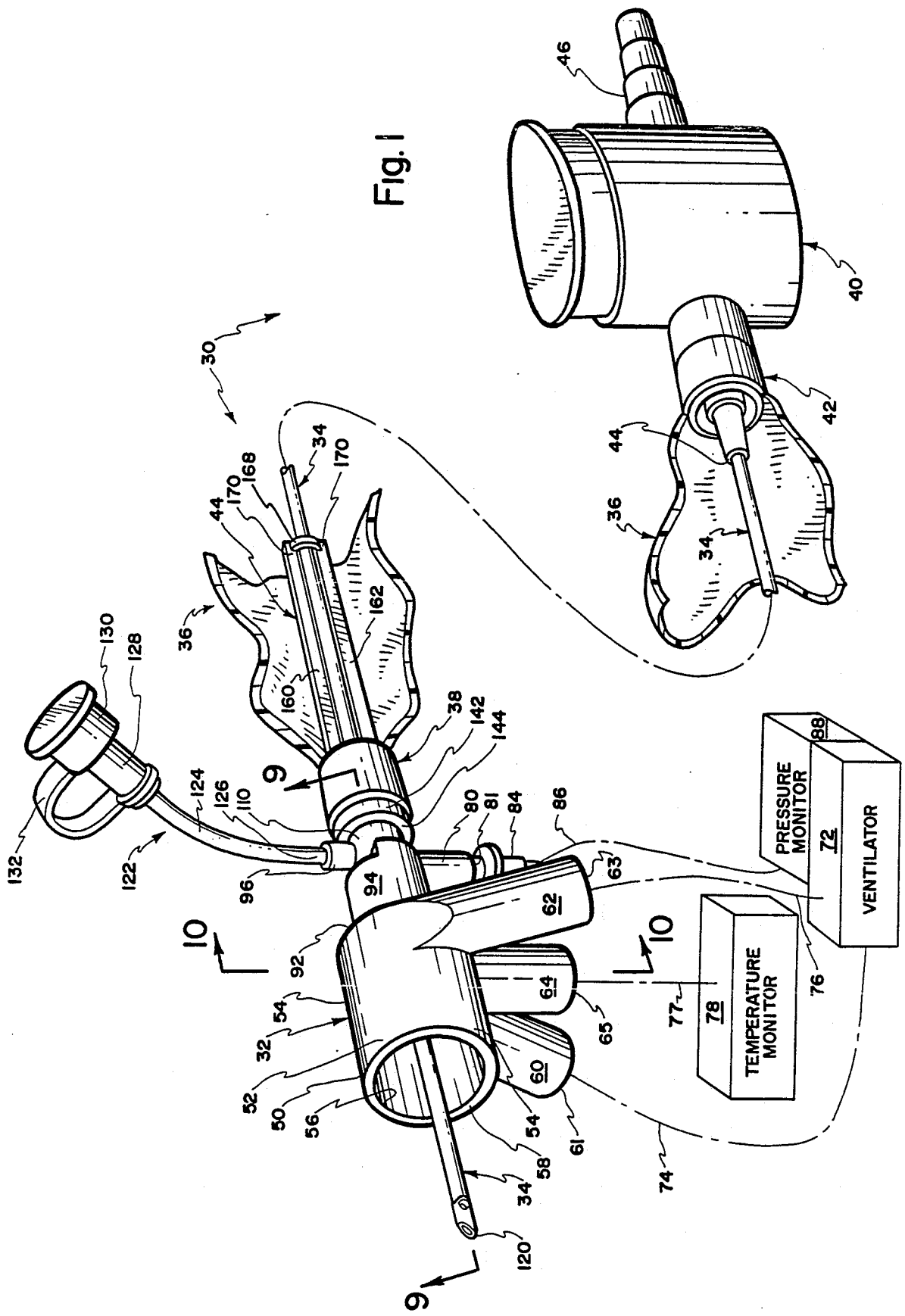
FIG. 1 is a fragmentary perspective of one presently preferred embodiment of the present invention.

Preferred embodiments of the present invention are illustrated in the drawings to which reference is now made and wherein like numerals are used to designate like parts throughout.

One presently preferred embodiment, comprising a ventilating/aspirating mechanism, is illustrated isometrically in FIG. 1 and is generally designated 30. The ventilating/aspirating mechanism 30 broadly comprises a ventilating/aspirating connector fitting 32, with which the apparatus 30 is connected to an exposed end of an indwelling endotracheal tube in press-fit, air-tight relationship. With the exception of fitting 32, apparatus is substantially similar to the apparatus disclosed in U.S. Pat. No. 4,569,344. The mechanism 30 thus also comprises a centrally disposed, axially directed suction catheter tube, generally designated 34, which is illustrated as being contained within a collapsible envelope, generally designated 36. The envelope 36 may be formed of synthetic resinous film in sleeve form, which is force-fit connected at collar 38 associated with the trailing end of the fitting 32 and also force-fit connected to a suction control valve 40 via collar 42 near the trailing end of the apparatus.

The catheter tube 34 is adapted to be displaced snugly through the fitting 32 and is rigidly anchored to the control valve 40 at site 44. Apparatus 30 further comprises the suction catheter tube insertion guide, generally designated 44. Insertion guide 44 is stationarily joined to the trailing end of the fitting 32.

The suction control valve 40 comprises a stepped hollow projection 46 by which the valve 40 is connected in fluid communication with a source of negative pressure, such as a conventional hospital suction system.

Specific reference is now made to FIGS. 1, 9 and 10 for the purpose of describing in greater detail the aspirating/ventilating fitting 32. Preferably, fitting 32 is of one piece molded construction, formed using conventional injection molding techniques. Fitting 32 may be transparent to permit visual observation of the interior thereof. The fitting 32 comprises a female barrel 50, which comprises a circular wall 52 illustrated as being of uniform thickness throughout, the barrel 50 comprising exterior and interior cylindrical wall surfaces 54 and 56, respectively. The leading edge 58 is blunt.

Thus, at the fore end of the fitting 32, the barrel 50 is of substantially uniform inside diameter, sized and shaped so that the interior of the barrel 50 will snugly match the female exposed connector of an indwelling endotracheal tube for press-fit connection in a substantially air-tight fashion. Such connection is intended not to interfere with the flow of ventilating air, or certain monitoring functions as hereinafter more fully explained.

The overall interior length of the female bore 56 is illustrated as being approximately one-half of the overall axial length of the connector fitting 32. The barrel or wall 52 is interrupted by three co-planer transversely-directed non-axial integral port structures 60, 62 and 64, each of which has a hollow cylindrical interior of uniform diameter throughout in open communication with the axially-directed fore bore 56 of the fitting 32, the open cylindrical interior thereof being identified respectively as 66, 68 and 70. The port structures each end in a blunt transverse end edge 61, 63 and 65 respectively. See FIG. 10.

The uniform cylindrical nature and the size of the hollow interior of each port structure 60, 62 and 64 accommodates press-fit reception of conventional male coupling members, the interior of the port structures 60 and 62 being illustrated as being connected to the input and output of a conventional ventilator 72 for ventilation ingess and egress (FIG. 1) by hollow conventional tubing, diagrammatically illustrated at 74 and 76, respectively. The hollow interior 70 of the port structure 64 is illustrated, in FIG. 1, as being connected to a conventional temperature monitor 78, for continuous monitoring of the respiratory temperature of the associated patient to accommodate immediate medical response to any temperature contraindication.

The port structures 60, 62 and 64 are closely juxtaposed one to the next and are downwardly directed toward the chest of the patient when the apparatus is in use. This is of particular significance for neonatal use as it eliminates or greatly alleviates inadvertent separation of the fitting 32 from the exposed fitting of an indwelling endotracheal tube or the connections to the ventilator or monitors. It also eliminates trauma induced by inadvertent displacement of the fitting 32 during the movement of the patient, as, for example, when bed clothing would otherwise be caught on projections of prior art fittings used to connect ventilating/aspirating apparatus to an indwelling endotracheal tube, etc.

The fitting 32, toward the trailing end thereof, has an additional downwardly directed port structure 80, having a hollow, cylindrical interior 82 into which a male fitting 84 (FIG. 1) is illustrated as being force fit and to which the trailing end a hollow tube 86, diagrammatically illustrated in FIG. 1, can be used to conventionally connect the port structure 80 to a conventional pressure monitor 88 which normally is part of the ventilator 72. The port structure 80 terminates in a blunt edge 81. With reference to FIG. 9, it is to be appreciated that the hollow cylindrical interior 82 of the port structure 80 connects on a 90 degree angular basis with a rectangular passageway 90 and thence with the hollow bore interior 56 of the barrel 50. Thus, the pressure of the infant or other patient can be continuously monitored to thereby accommodate immediate response to any pressure contraindication.

It is to be appreciated that in the event that the apparatus 30, with the fitting 32 in place, is used with certain types of equipment existing in various medical facilities not having pressure monitoring or temperature monitoring capacity, the hollow interior of the port structure 64 and 80 can be selectively plugged with a removal plug.

The fitting 32, as best illustrated in FIG. 9, comprises an arcuate or curvilinear shoulder 92 adjacent the top region of the wall surface 54, at the trailing end thereof which merges with an arcuate exposed surface 94 of reduced diameter. Surface 94 merges with an upwardly projecting hollow circular boss 96, the interior surface 98 of which has a uniform diameter. The uniform bore 98 extends transversely from the exterior to a relatively small interior axial bore 100 disposed near the aft end of the fitting 32. The axial bore 100 is sized and shaped so as to snugly accommodate linear passage of the suction catheter tube 34 therethrough in such a way as to create a substantially sealed relationship at site 101 between the exterior of the catheter 34 and the bore 100. This prevents inflation or deflation of the interior of the envelope 36.

The bore 100 comprises part of a body of material 102, which has a forward tapered leading surface 104 and is joined to the trailing end of the barrel 50, of wall 93. The body of material 102 merges with a rearwardly directed hollow annulus 106 which comprises a circular wall of uniform thickness defining an interior cylindrical surface 108 and an exterior cylindrical surface 110. The interior surface 108 merges with the much smaller axial bore 100 at tapered counterbore 112. The tapered surface of counterbore 112 deflects the leading end 120 (FIG. 1) of the suction catheter tube 34 when contact therebetween is made during catheter tube advancement. This catheter tube tip 120 deflection brings the tip 120 into alignment with the bore 100.

The exterior surface 110 of the annulus 106 accommodates connection between the fitting 32 and the insertion guide 44, in a manner hereinafter more fully described.

A catheter tube wash structure 122 is connected to the fitting 32 within the upwardly directed bore 98. More specifically, the structure 122 comprises a flexible hollow tube 124, the outside diameter of which is substantially the same as the diameter of the bore 98. The one end of the tube 124 is caused to be advanced into the bore 98 after the end 126 is coated with a suitable adhesive or bonding agent. Thus, the end 126 of the tube 124 becomes integrally joined to the surface forming the bore 98 of the fitting 32.

The tube 124 integrally merges with a larger female fitting 128, which is normally closed by a cap 130 press-fit upon the female fitting 128. The cap 130 is tethered at 132 to the fitting 128 so that the cap 130 does not become lost when it is removed and wash solution is caused to be passed under pressure through the fitting 128 and the tube 120 to wash the exterior of the catheter tube 34 as it is withdrawn from the respiratory system of the patient and to wash the interior of the catheter tube when fully withdrawn. This procedure is described in greater detail in U.S. Pat. No. 4,569,344. This procedure removes all secretions which would otherwise remain upon the exterior and interior surfaces of the catheter tube 34 after withdrawal.

The flexible nature of the tubing 124 allows the structure 122 to flex readily when contacted by the patient, the clothing of the patient or the like so that snagging does not occur and the apparatus 30 is not inadvertently disconnected in any way and trauma which would otherwise be induced by displacement of the apparatus 30 is avoided.

Specific reference is now made to FIGS. 1 through 5 for purposes of describing the insertion guide 44 in detail. As can be seen from FIG. 3, the insertion guide 44 is disposed, in the assembled condition, internal of the plastic envelope 36 in such a way that the suction catheter tube 34 is loosely centrally disposed therethrough.

The leading end of the insertion guide 44 comprises a hollow stepped sleeve, generally designated 140. See FIG. 2. Sleeve 140 comprises an enlarged collar 142 at the leading tip thereof. Collar 142 is cylindrical and of uniform thickness. Collar 142 comprises a blunt end 144 and a uniform interior diameter at surface 146. The diameter of surface 146 (FIG. 2) is substantially the same as the diameter of the exterior surface 110 of the fitting 32. Consequently, by interposing a suitable adhesive or bonding agent between the surface 110 and the surface 146 and superimposing 110 over 146, the insertion guide 44 is integrally and stationarily joined to the fitting 32. As such, guide 44 extends rearwardly in cantilevered relationship. See FIG. 1.

The collar 142 is internally stepped at shoulder 148 and externally stepped at shoulder 150 to form reduced diameter inside and outside cylindrical segment comprising surfaces 152 and 154. The internal bore formed by surface 152 is further reduced at internal shoulder 153 whereby cylindrical surface 155 results. Reduced bore 155 is followed by counterbore 157. Counterbore 157 terminates in a constriction at orifice 159, the diameter of which is slightly larger than the outside diameter of the tube 34.

The exterior cylindrical surface 154 is interrupted just forward of the trailing shoulder 156 by an annular radially extending rib 158.

The insertion guide 44 is preferably formed of a suitable synthetic resinous material fabricated in one piece using conventional injection molding techniques. The insertion guide 44 further comprises top and bottom longitudinally-directed beam members 160 and 162, each of which is illustrated as being rectangular in cross-section and identical one to another. The leading end 164 and 166 of each is integrally joined to the trailing end of the sleeve 140 adjacent counterbore 157 and shoulder 156. Each beam member 160 and 162 extends rearwardly for a distance of several centimeters. For example, the inserter guide 44 may be five centimeters in length. Of course, other lengths could be used, depending upon the overall size of the ventilating/aspirating apparatus among other things.

The beams 160 and 162 are thus parallel to, but respectively oppositely offset from the axis of the sleeve 140 and the fitting 32 through which the suction catheter tube 34 is advanced into a desired lung of the patient where accumulated lung secretions are to be removed. The parallel beam members 160 and 162 are joined one to another by an integral ring 168 disposed at the trailing end 170 thereof. The ring 168 has a blunt leading edge 172 and a blunt trailing edge 174. The exterior diameter of the ring 168 is illustrated as being less than the diameter of the sleeve portion 154 while the internal diameter at surface 176 of the ring 174 is illustrated as being substantially the same as the distance between the beam members 160 and 162.

With the annular collar 38 force-fit securing the leading end of the collapsible plastic envelope 36 to the surface 154 of the sleeve 140 (by placing the annular projection 150 between two inwardly directed projections on the interior surface of the collar 38 as explained in U.S. Pat. No. 4,569,344, and the apparatus 30 otherwise assembled in its ready-to-use condition, the user, as illustrated in FIG. 3, firmly grips the plastic envelope 36 at the opposed exterior side surfaces thereof tightly against the exterior surface of the suction catheter tube 32. Preferably the outside diameter of the catheter tube 32 is wider than the width of the beam at members 160 and 162.

Thereafter, the user advances the suction catheter tube 34 and the exterior envelope 36 axially slidably along the guide 44, through the fitting 32 and the indwelling endotracheal tube into a desired location within the respiratory system of the patient. It should be clear that while the external envelope 36 and the catheter tube 34 are held tightly and advanced by the fingers of the user, the engagement of the bars 160 and 162 between the fingers is slidable and accommodates a linear advance of the envelope 36 and the tube 32 parallel to the stationary bars 160 and 162.

The advancing step is repeated as many times as necessary to insert a desired length of catheter tube into a selected lung of the patient and position the same so that accumulated secretions within the lung can be evacuated by negative pressure communicated through the suction catheter tube 34 when the control valve 40 is activated without injury to the patient. It should, therefore, be appreciated that the insertion guide 44 provides for facile and accurate placement of the catheter tube 34 in the respiratory system of a patient and is particularly helpful to avoid lung damage when the patient is an infant or child.

Preferably, the control valve 40 is preferably identical or substantially identical to the control valve described in U.S. Pat. No. 4,569,344, as is the male coupling member 46, the connection site 44, the collar 42. No further description is believed to be necessary in regard to the control valve 40 and the indicated adjacent structure, the disclosure of U.S. Pat. No. 4,569,344 being incorporated herein by reference.

Reference is now made to FIGS. 6-8, which illustrate a further embodiment of the present invention, i.e. an insertion control device, generally designated 180, for restricting to a predetermined length the amount of the suction catheter tube 34 which is available to be inserted into the respiratory system of a patient. This prevents occlusion due to kinking, and lung damage by reason of excessive insertion, which would otherwise risk puncturing the lung of an infant.

The insertion control mechanism 180 comprises a sleeve 182 and a collar 184. The sleeve 182 is illustrated as having a radial flange 184' at one end interposed between a blunt forward edge 186 and a shoulder 188. The flange 184' is centrally hollow, the hollow forming part of an internal axial bore 190 of uniform dimension throughout, the unstressed diameter of which is only slightly greater than the exterior diameter of the catheter tube 34. Thus, the sleeve 182 can be axially displaced relative to the catheter tube 34 when the sleeve 182 is unstressed and superimposed telescopically upon the catheter tube 34.

The flange 184' merges with a rearwardly directed ring segment 192. Ring segment terminates at blunt traverse edge 197. The bore 190 expands through the ring 192 so that it spans the full length of the sleeve 182. The ring 182 has a rearwardly convergent circular exterior surface 194, for purposes hereinafter more fully described. A pair of aligned slots 196 span from the blunt end surface 186 rearwardly across the entirety of the flange 184' and a substantial distance along each side of the ring 192, for purposes hereinafter more fully explained.

The collar 184 is illustrated as being of relatively short length and comprises an exterior annular surface 198 and blunt forward and rearward edges 200 and 202. The diameter of the exterior surface 198 is illustrated as being slightly greater than the diameter of the flange 184'. See FIG. 6, which comprises a side elevation view of the assembled insertion control device 180. The collar 184 comprises an axial throughbore 204 which tapers divergently from left to right, as viewed in FIG. 7.

The bore 204 is sized and shaped so that the diameter thereof adjacent surface 200 is slightly greater than the diameter of the ring 192 at the trailing end 197 so that the collar 184 can be readily advanced telescopically upon the ring 192. The bore 204 is sized and shaped so that the diameter thereof adjacent trailing edge 202 of collar 184 is somewhat less than the unstressed diameter of the ring 192 directly adjacent the shoulder 188. Consequently, when the collar 184 is fully advanced telescopically upon the ring 192 into the assembled position illustrated in FIG. 6, the collar 184 compresses the ring 192 and the collar 184 adjacent the shoulder 188 thereby closing or tending to close the two opposed slots 196. This causes the ring 192 and the collar 184 to pinch or compressively engage the exterior surface of the suction catheter tube 34 to the extent that relative axial movement of the insertion control device 180 along the catheter tube 34 cannot occur thereafter.

To install the insertion control 180, the separated sleeve 182 and collar 184 are advanced sequentially along the exterior surface of the suction catheter tube 34 until the sleeve 182 is at a desired location along the catheter tube. This location can be ascertained by measurement or by placing length indicia on the exterior of the suction catheter tube, as illustrated in FIGS. 2 and 6. When the sleeve 182 has been placed in superposition upon the suction catheter tube 34 and displaced to the desired location, the collar 184 is force-fit upon the ring 192 forcing the insertion control device 180 into the assembled locked position illustrated in FIG. 6. The insertion control device 180 is illustrated as being located about 22 centimeters to the rear of the tip 120 of the suction catheter tube 34.

As a consequence, when the catheter tube 34 is advanced into the respiratory system of a patient, the forward edge 186 will ultimately come in contact with some other stationary part of the apparatus 30, such as the fitting 32. In the alternative, if the insertion guide 44 is also used, the ring 168 thereof will form a stationary stop against which the forward edge 168 of the control device 180 will abut to prevent further insertion of the suction catheter tube 34. See FIG. 8.

It is to be appreciated that the insertion control device 180 may be subsequently telescopically separated into its components and relocated to a different position should medical personnel choose to use a longer or shorter length of suction catheter tube in the respiratory system of a patient.

Reference is now made in FIGS. 11 through 14 which illustrate a further embodiment of the present invention, more particularly an adaptor for interpositioning between an exposed fitting 218 of indwelling endotracheal tube and an aspirating apparatus or ventilating/aspirating apparatus. It is to be appreciated that the adaptor in question, generally designated 210, can interconnect an endotracheal tube with, for example, a single-use aspirating device, or a multiple use aspirating-/ventilating device. Such connection is diagrammatically illustrated at female fitting 212 in FIG. 11.

The structure and placement of the endotracheal tube 214, illustrated in FIG. 11, is conventional. The endotracheal tube 214 is conventional and comprises an exposed proximal end 218.

The adaptor 210 is best shown in FIGS. 12-14, in reverse orientation. The adaptor 210 comprises a central exposed radial flange 220 which defines opposed shoulders 222 and 224. The flange 220 merges integrally with a rearward extension 226, which defines a cylindrical exterior exposed surface 228 to receive an aspirating or aspirating/ventilating apparatus at an appropriate fitting thereof in snug force-fit air-tight relation. The extension 226 comprises a trailing blunt edge 229, which merges into a conically-shaped counterbore 230, which in turn emerges with a central axially-directed bore 232. The purpose of the tapered counterbore 230 is to deflect the leading end of a suction catheter tube associated with the aspirating or aspirating/ventilating apparatus connected to the adaptor 210 so as to direct the tip into and through the central bore 232 when the tube 34 is being placed in the respiratory system. The bore 232 is sized and shaped so as to receive the suction catheter tube when the same is co-axially advanced therethrough and to accommodate a force-fit union between the surface 236 and the interior of the exposed end of the endotracheal tube.

The adaptor 210 further comprises a forwardly directed male tip 234 through which the bore 232 also axially passes. The exterior surface 236 of the male tip 234 is forwardly divergently tapered and otherwise sized and shaped to be snugly received in air-tight relation within the exposed end 218 of the endotracheal tube 214, whereby the suction catheter tube passing through the bore 232 of the fitting 210 will be caused to be directed into the hollow interior of the endotracheal tube 214 and thence into the respiratory system of the patient 238.

The extension 226 comprises cavities 240 to eliminate use of unnecessary synthetic resinous material when the adaptor 210 is preferably formed as one piece using injection molding techniques. For strength, however, radial flanges 242 exist between the cavities 240.

The axial bore 232 is interrupted and intersected openly by transverse bore 244 (FIG. 13). The bore 244 is formed in the flange 220 and includes a stepped counter-bore portion 246 slightly greater in interior diameter than the bore 244 but essentially equal to the outside diameter of a hollow plastic tube 248 which is placed in the counterbore 246 and adhesively or bondedly retained therein. The tube 248 is connected at site 250 with a female sleeve fitting 252. The female fitting 252 is normally closed by a press-fit cap 254 integtral therewith by reason of a tether 256.

With the endotracheal tube 214 indwelling, the adaptor 210 press-fit into the exposed end 218 of the endotracheal tube, the aspirating apparatus comprising fitting 212 secured to the adaptor 210 and the suction catheter tube of the aspirating apparatus withdrawn, medical personnel can selectively remove the cap 254 and selectively inject a lavage solution of proper makeup and dilution through the female fitting 254, the hollow interior of the tube 248, the bore 232 and thence down the endotracheal tube 214 into the lungs of the patient for purposes of loosening accumulated secretions in the lungs. This accommodates subsequent removal of the loosened secretions via the mentioned suction catheter tube when appropriately inserted into the lungs of the patient.

The flange 220 is illustrated as comprising opposed outwardly directed tabs 258, sized and shaped so that the adaptor 210 may be easily manually manipulated.

Specific reference is now made in FIGS. 15-19, which illustrates a further embodiment of the present invention, i.e. an observation chamber generally designated 270 interposed in the suction catheter tube flow path between the trailing end of the envelope 36 of apparatus 30' and the suction control valve 40.

As stated earlier, the suction control valve 40 is known in the art and is disclosed in the U.S. Pat. No. 4,569,344. Control valve 40, as best illustrated in FIG. 16, comprises a female recess 272 sized and shaped for appropriate fluid communication connection to the secretion observation chamber 270. The apparatus 30' comprises the heretofore described, collapsible envelope 36, suction catheter 34 and connector 44, integrally joined to the trailing end of the catheter tube 34. The fitting 44 integrally joins a fitting, generally designated 274. The fitting 274 comprises a forwardly projecting extension 276 which comprises the cylindrical exterior of predetermined diameter interrupted by an annular radially extending rib 278. The envelope 36, at the trailing end thereof, is collapsed into contiguous relation with the cylindrical surface 276, with a collar 280 disposed in surrounding relation to the envelope 36 but forwardly offset from the surface 276.

The collar 280 is annular in its configuration defining a cylindrical exterior surface 282 having a diameter slightly larger than the diameter of the cylindrical surface 276 of the fitting 274. The internal surface 284 of the collar 280 is interrupted by spaced ribs 286. The diameter of the surface 284 and the annular ribs 286, which project radially inwardly, are sized and shaped so that forced advancement of the collar 280 over the trailing end of the envelope 36 into superposition with the cylindrical surface 276 creates a force-fit connection between the fitting 274 and the trailing end of the envelope 36 between ribs 286 and 278. The cylindrical surface 276 of the fitting 274 comprises part of an annular wall 290 (FIG. 17) which also defines an annular interior wall surface 292.

Concentric with the wall 290 is a wall 294, illustrated as having uniform thickness defining an exterior cylindrical surface 296 and an interior cylindrical surface 298. The fitting 44 integrally carried at the trailing end of the suction catheter tube 34 is sized and shaped to snugly fit within wall 294 at surface 298 where it is adhesively or otherwise stationarily secured against inadvertent separation. Thus, the hollow bore at 300 is placed in direct fluid communication with the hollow interior of the suction catheter tube 34.

The fitting is illustrated as comprising a construction at orifice at 302, which comprises a forward shoulder 304 and a larger rearwardly directed shoulder 306. Thus, the central bore is enlarged at bore 308 which is disposed at the trailing end of the fitting 274.

The exterior cylindrical surface 276 merges at shoulder 310 with an exterior cylindrical surface 312 of larger diameter. The cylindrical surface 312 comprises wall 314 which is of uniform thickness and defines also an internal cylindrical or annular surface 316. Shoulder 306 merges with an annular projection 318, which comprises an exterior cylindrical surface 320 and an interior cylindrical surface 322. Cylindrical surface 322 defines the enlarged bore section 308. The diameter of the exterior surface 320 is substantially smaller than the diameter of the cylindrical surface 316 thereby defining an annular recess 324 therebetween. Radial strengthening ribs 326 span between the walls 314 and 318 to provide strength and stability, as best shown in FIG. 19.

The observation chamber 270 is tubular and has a funnel shape. Thus, the observation chamber 270 is both interiorly and exteriorly tapered. Observation chamber 270 comprises a length of transparent tubing of the mentioned tapered configuration 332. The tubing 332 is centrally hollow, defining a central bore 334, which has a diverging configuration from left to right. The wall 332 is of substantially uniform thickness throughout, with the exception that a cylindrical seat 336 is defined at the larger leading end at the interior thereof. The cylindrical seat 336 extends from the blunt leading edge 338 of the tubing 332 to an interior annular shoulder 340. The diameter of the annular seat 336 is substantially the same as the diameter of the cylindrical surface 320 of the fitting 274. Thus, by placing a suitable bonding agent or adhesive between the rearward portion of surface 320 and/or the surface defining the seat 336, joining of the fitting, at projection 318 with the tapered tubing 332 is made permanent and inseparable.

The observation chamber 270 comprising tube 332 is transparent, preferably formed of acrylic of medical grade. The taper of the bore 334 provides for initial introduction of the secretions withdrawn from the lungs of a patient through the suction catheter tube 34 to flow slowly into the observation chamber 270 and more rapidly thereafter for accurate visual observation of the rate of flow of the secretions, the approximate quantity of the flow, as well as the color, texture and other characteristics of the secretions. The wall 332, at the trailing end, defines a cylindrical surface 342, which terminates in a blunt transverse edge 344. The diameter of the surface 342 is selected to be substantially the same as the diameter of the recess 272 in the suction control valve 40 so that a bonding agent may be interposed between the two and the two interposed in contiguous relation to create a permanent union therebetween.

The invention may be embodied in other specific forms without department from the spirit or essential characteristics thereof. The present embodiments, are, therefore, to be considered in all respects as illustrative and not restrictive, the scope of the invention being indicated by the appended claims rather than by the foregoing description, and all changes which come within the meaning and range of equivalence of the claims are therefore to be embraced therein.

What is claimed and desired to be secured by United States Letters Patent is:

1. A ventilating/aspirating apparatus for neonatal respiratory therapy comprising:
connector fitting means disposed at one end of the apparatus for selective connection to an indwelling endotracheal tube fore and aft axial bore means, the aft bore means accommodating selective passage of a suction catheter tube into and through the fitting, the endotracheal tube and into a selected lung of a patient, the fore bore means accommodating said passage of the suction catheter tube and involuntary ventilation of the patient as well;
the connector fitting means further comprising non-axial low dead space ingress ventilating port means and egress ventilating port means by which ventilating gases are displaced to and from the lungs of the patient via the endotracheal tube and the fore bore means and the ingress and egress ventilation port means, the ingress and egress ventilation port means being closely juxtaposed one to the other and projecting away from the fore and aft axial bore means in side-by-side relation whereby ventilating connections made to the ventilation port means are made from substantially the same direction providing connecting tube paths away from the patient by which incidents of inadvertent disconnection and trauma induced by unintended displacement of the fitting are alleviated;

the fore axial bore means comprising means by which the exposed end of the endotracheal tube and the apparatus are caused to be operatively joined.

2. An apparatus according to claim 1 further comprising non-axial laterally oriented port means for selectively introducing a solution into the interior of the connector fitting means to wash the exterior and interior of the suction catheter tube as and after it is withdrawn from the respiratory system of the patient through the endotracheal tube and the connector fitting means.

3. An apparatus according to claim 1 wherein the ventilating ingress and egress port means and at least one monitoring connection means are disposed in generally side-by-side relationship in a common plane, closely juxtaposed one to another, essentially transverse to the axis of the connector fitting means whereby incidents of inadvertent disconnection and trauma during use, induced by unintended displacement of the fitting, are alleviated.

4. An apparatus according to claim 1 wherein the fore axial bore means accommodate force-fit installation in association with an exposed end of the indwelling endotracheal tube.

5. An apparatus according to claim 1 wherein the aft axial bore means accommodate assembly of the connector fitting means with the remainder of the apparatus.

6. An apparatus according to claim 1 wherein the connector fitting means are internally sized and shaped to form a snug sealed relationship with the suction catheter tube when the two are co-extensively disposed.

7. An apparatus according to claim 1 wherein seal means are disposed within the connector fitting means sized and shaped to snugly form a sealed relationship with the exterior surface of the suction catheter tube when stationarily disposed within and when being displaced through the connector fitting means.

8. A ventilating/aspirating apparatus useful for neonatal respiratory therapy comprising:

connector fitting means disposed at one end of the apparatus for selective connection to an indwelling endotracheal tube comprising fore and aft axial bore means, the aft bore means accommodating selective passage of a suction catheter tube into and through the fitting, the endotracheal tube and into a selected lung of a patient, the fore bore means accommodating said passage of the suction catheter tube and involuntary ventilation of the patient as well;

the connector fitting means further comprising non-axial ventilation ingress and egress means by which ventilating gases are displaced to and from the lungs of the patient via the endotracheal tube and the fore bore means and the ingress and egress means, the ingress and egress means being closely juxtaposed one to the other and projecting away from the fore and aft axial bore means;

the fore axial bore means comprising means by which the exposed end of the endotracheal tube and the apparatus are cause to be operatively joined.

non-axial monitoring port means by which, when in an installed operating condition, selected vital conditions of the patient are continuously monitored.

9. An apparatus according to claim 8 wherein the monitoring port means comprise port means for monitoring pressure and temperature conditions of the patient.

* * * * *